United States Patent [19]
Lipson

[11] Patent Number: 5,312,114
[45] Date of Patent: May 17, 1994

[54] APPARATUS AND METHOD FOR ENHANCING DECISION-MAKING

[76] Inventor: Warren M. Lipson, 9701 Yoakum Dr., Beverly Hills, Calif. 90210

[21] Appl. No.: 983,460

[22] Filed: Nov. 30, 1992

[51] Int. Cl.$^5$ .......................... A63F 9/22; G09B 7/00
[52] U.S. Cl. .................................. 273/434; 273/429; 434/236; 434/307; 434/323
[58] Field of Search ............... 273/429, 430, 431, 432, 273/434, 435, 436; 434/236, 237, 322, 323, 326, 319, 320, 321, 308

[56] References Cited

U.S. PATENT DOCUMENTS

| | | | |
|---|---|---|---|
| 4,078,316 | 3/1978 | Freeman | 434/319 |
| 4,300,763 | 11/1981 | Barr | 434/236 X |
| 4,717,343 | 1/1988 | Densky | 434/236 |
| 4,734,038 | 3/1988 | Dennis | 434/236 |
| 4,762,494 | 8/1988 | Woods | 434/236 |
| 4,812,126 | 3/1989 | Gilliksen | 434/238 |
| 4,900,256 | 2/1990 | Dara-Abrams | 434/236 |
| 4,923,428 | 5/1990 | Curran | 446/175 |
| 4,931,934 | 6/1990 | Snyder | 434/236 X |
| 5,026,051 | 6/1991 | Lowe et al. | 273/435 |

Primary Examiner—William H. Grieb
Attorney, Agent, or Firm—W. Edward Johansen

[57] ABSTRACT

An apparatus and a method for enhancing decision-making using left to right to left hemisphere guidance includes a housing, two buttons which are coupled to the housing and four recording media with their respective instructions to a user. The first instruction is to think about a subject until an issue related to the subject comes to his mind, then to make a choice from alternatives of the issue and thereafter the user presses one of the two buttons to designate his choice of one of the alternatives of the issue. The second instruction is to look inside his head and ask himself if he is right while he is inclined to a new discovery. The third instruction is to see a picture of the subject in his head and while he is daydreaming the picture to listen for thoughts in his mind about how he is right, then to listen for thoughts in his mind about the other side of the issue, with both sides of the issue in his mind to listen for changes over a period of time. The fourth instruction is to verbalize his conclusions.

8 Claims, 3 Drawing Sheets

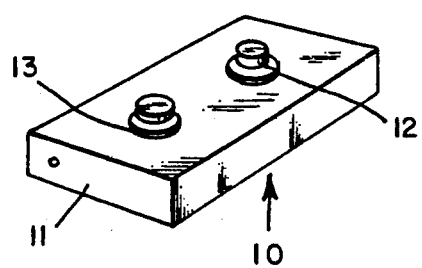
Fig. 1.
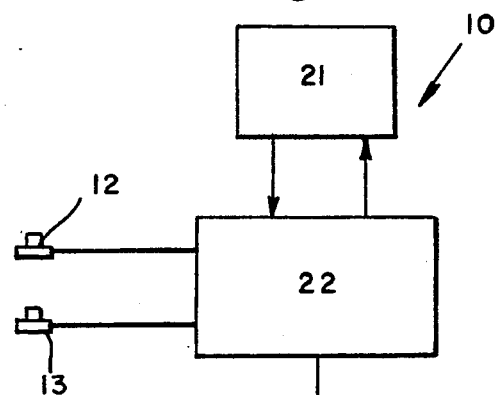
Fig. 2.
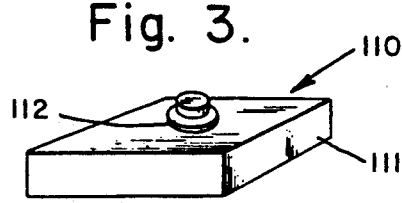
Fig. 3.
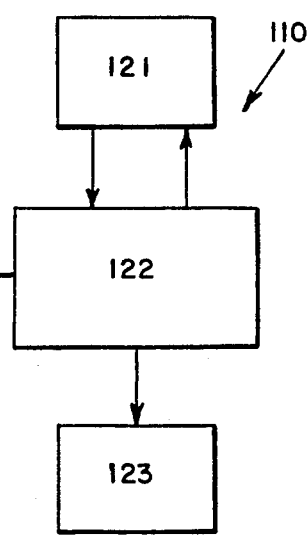
Fig. 4.
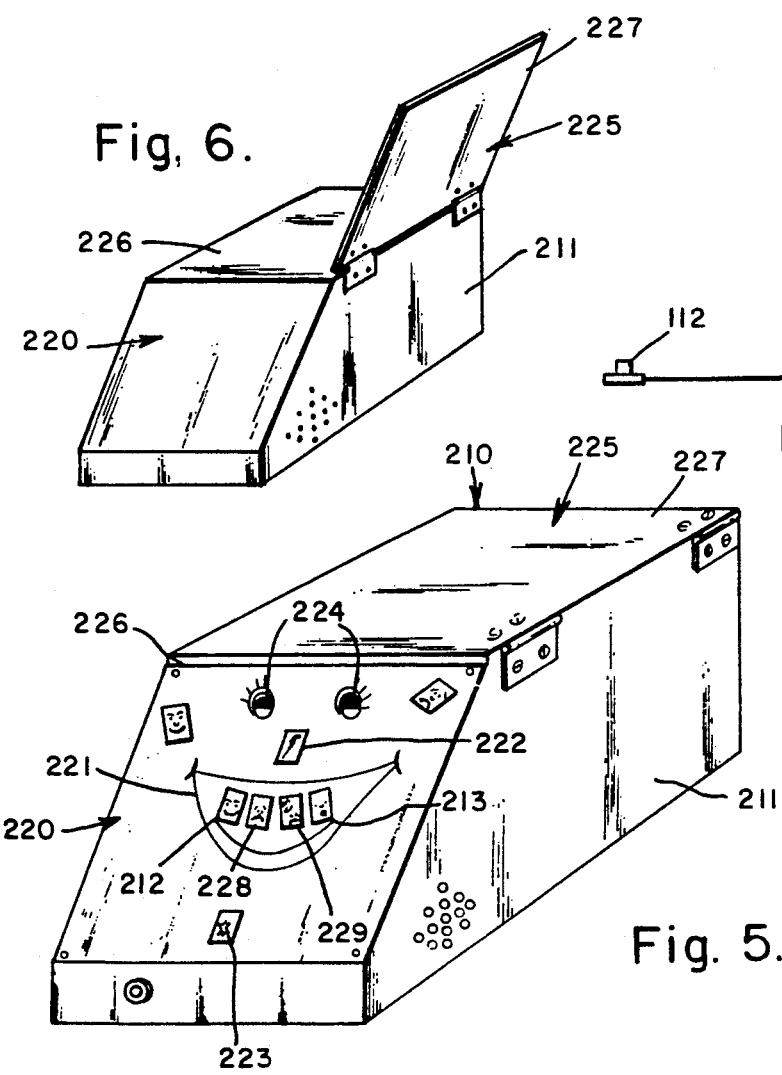
Fig. 6.
Fig. 5.

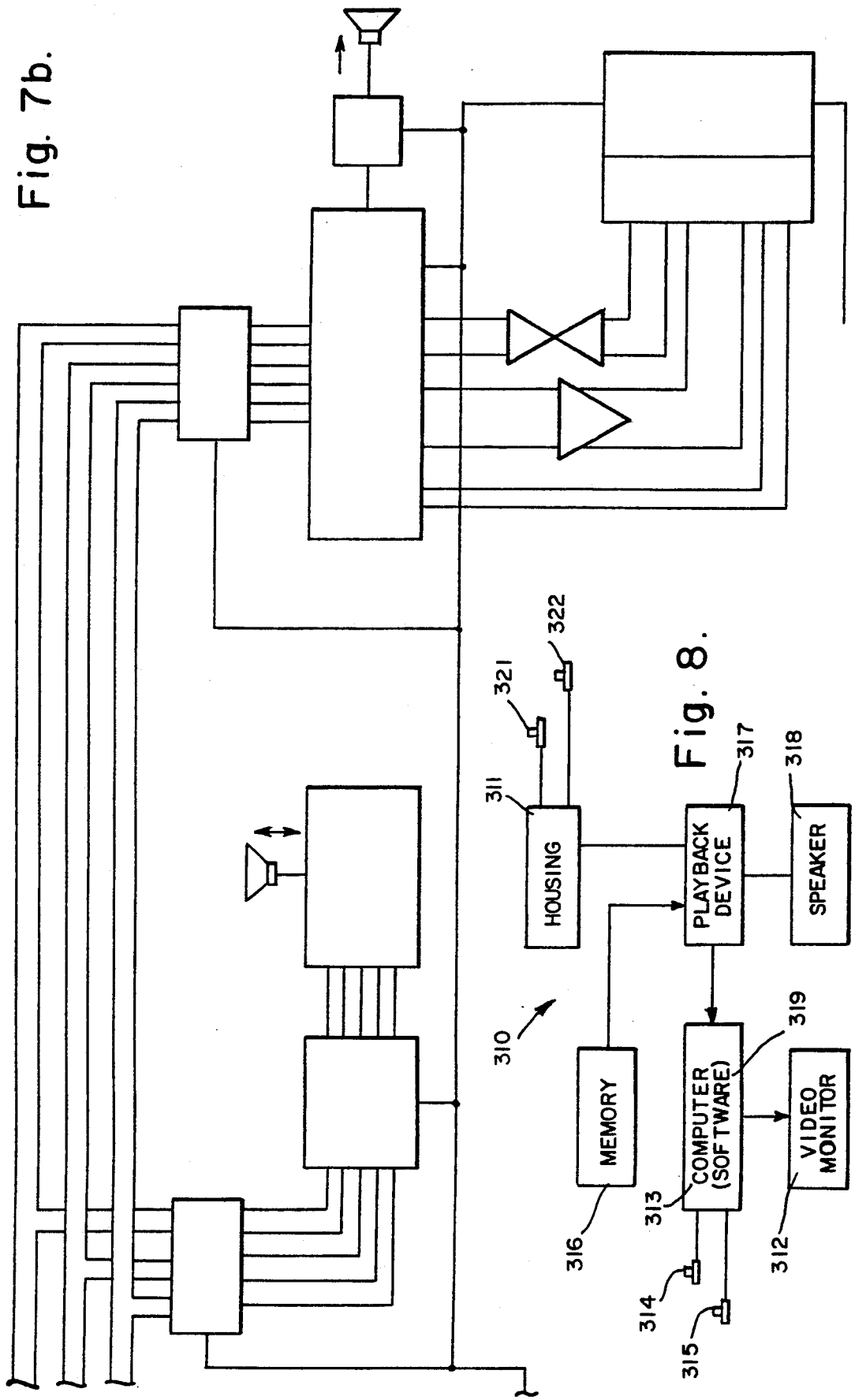

APPARATUS AND METHOD FOR ENHANCING DECISION-MAKING

BACKGROUND OF THE INVENTION

The field of the invention is psychological devices for enhancing the making of decisions.

U.S. Pat. No. 4,900,256 teaches an object-directed emotional resolution apparatus which uses speech and electronics technology coupled with psychological techniques to further emotional development and stress reduction.

U.S. Pat. No. 4,923,428 teaches an interactive, articulated talking toy which talks and moves certain of its body parts under microprocessor control on the basis of the program material selected from a tape storage device incorporated in the body of the toy. The material selected is determined by a human's response to questions asked by the toy. The material stored on tape contains both audio and data. The processor chooses a particular one of a possible three audio tracks stored on tape on the basis of the specific response or nonresponse made by a human.

U.S. Pat. No. 4,300,763 teaches a psychological game device having a small box-like housing which has cabinet with a panel facing a player called the SPEAKER and another panel facing a player called the LISTENER. The SPEAKER panel mounts two push buttons labeled TRUTH and ALMOST TRUTH. The LISTENER panel mounts two push buttons labeled BELIEVE and ALMOST BELIEVE. The bottom of the cabinet includes a recessed panel with scoring indicators labeled CREDIBLE consisting of three light emitting diodes (LEDs) and FORGET-IT consisting of three LEDs. A reset button is also provided. The top surface of the cabinet contains an on/off switch, a START push-button, and an LED indicator. A timer circuit, started by the START button, illuminates the indicator LED for either a preselected time period or a sequence of random duration time periods. Logic circuits contained within the cabinet are controlled by the SPEAKER and LISTENER push buttons to provide a basic game sequence of three periods. The device may be used with a wide variety of games limited only by the imagination of the players.

U.S. Pat. No. 4,717,343 teaches a method of conditioning a person's unconscious mind in order to effect desired change in the person's behavior which does not require the services of a trained therapist. The program as viewed by the person's unconscious mind acts to condition the person's thought patterns in a manner which alters that person's behavior in a positive way.

U.S. Pat. No. 4,762,494 teaches a psychotherapy 9 device which includes a body member, a pair of arms, legs, and a head connected to the body member. The pyschotherapy device is in the general configuration of a child-like human figure. The head includes a pair of expressionless eyes and nose which are permanently affixed to the face and means are connected to the face adjacent to and generally below each of the permanent eyes for releasably receiving indicia of tears. During pyschotherapy of a child patient, the patient may be invited to apply or remove tears to reflect a current or past mental state.

U.S. Pat. No. 4,812,126 teaches a new method of learning by use of a machine which interacts with the user to guide the user through a programmed series of questions. The system is based on finding trouble spots in the users logic or feelings by observing the users skin response to questions. The computer will ask the user a question. The computer selects the next question based on his answer to the previous question and guides the use through a U.S. Pat. No. 4,931,934 teaches a system and method for measuring the emotional response of a subject to a chosen focus in order to reliably produce objective data representing that emotional response. The subject is put in contact with the chosen focus and the emotional response of that subject to the chosen focus is determined in order to provide initial response emotions and the intensities of these emotions. Utilizing the initial response emotion intensities and the baseline emotion intensities, clarified emotion intensities are determined for use in a variety of decision making applications.

U.S. Pat. No. 4,734,038 teaches a method which includes selecting the particular ideal behavior to be achieved, defining the steps to be taken to effectuate the modification, assigning a mnemonic device for each step to promote mental identification of the step and providing a visual image of a role model for behavioral emulation. The role model acts out the defined steps.

SUMMARY OF INVENTION

The present invention is directed to an apparatus and a method for enhancing decision-making using left to right to left hemisphere guidance which includes a housing and at least one button coupled to the housing.

In a first aspect of the present invention the apparatus includes a first recording medium with an instruction to a user to think about a subject until a first idea and a second idea, which is opposite to the first idea, related to the subject comes to his mind, then to make a choice between the first and second ideas. Thereafter the user presses one of the two buttons to designate his choice.

In a second aspect of the present invention the apparatus also includes a second recording medium with an instruction to the user to look inside his head and ask himself if he is right while he is inclined to a new discovery.

In a third aspect of the present invention the apparatus further includes a third recording medium with an instruction to the user to see a picture of the subject in his head and while he is daydreaming the picture to listen for thoughts in his mind about how he is right, then to listen for thoughts in his mind about the other side of the issue, then with both sides of the issue in his mind to listen for changes over a period of time.

In a fourth aspect of the present invention the apparatus still further includes a fourth recording medium with an instruction to the user to verbalize at least one of his conclusions.

In a fifth aspect of the present invention the two buttons are designated by a pair of opposite words from a group of pairs of opposite words consisting of positive and negative, good and bad, yes and no, you and I, past and future, up and down, know and do not know, accept and reject, right and wrong, like and dislike, should and should not, will and will not, can and can not.

In a sixth aspect of the present invention the apparatus yet further includes a recording medium and a voice playback device. The voice playback device receives the first, second, third and fourth recording media in order to playback their respective instructions.

In a seventh aspect of the present invention the apparatus guides a user who is uncomfortable to think about any subject long enough to realize any opposite ideas about the subject to nonetheless interact with the apparatus by simply considering his subject until any thought that is meaningful to him comes to his mind.

In a eighth aspect of the present invention the apparatus includes two other buttons in addition to the two oppositely designated buttons so that a user who is unable or unwilling to choose between the first idea and the second idea may nonetheless interact with the apparatus by simply selecting from the two other buttons. These designations may indicate a range between the two opposite designations, a combination of the two opposite designations or an inability or an unwilliness for the user to either choose or decide between the first idea and the second idea.

In a ninth aspect of the present invention the apparatus guides a user so that he opens his mind to both sides of his feelings and to changes in his feelings over a period of time.

In a tenth aspect of the present invention the apparatus is coupled to a video game which includes a start button, monitor and stop button. The start button is electrically coupled to the apparatus so that a user can enliven his feelings for playing the video game. The user is instructed to put a picture of an object from the video game in his head and to daydream playing the video game as action commences on the monitor. After repetitively pressing the start button before each play of the video game the user develops a habit of daydreaming what he is observing thereby becoming empathic for situations and people in unfolding events. The stop button is electrically connected to the apparatus so that the user can think through what he is going to do next after he quits playing the video game so that he realizes a balanced attitude about it. When pressing the stop button the user is instructed to think about what he is going to do next, then to make a thought about it, then to ask, image and listen about it in accordance with the aspects of this invention.

In an eleventh aspect of the present invention the apparatus guides a user through a process of relaxation so that the user may either think or feel about one subject at a time.

In a twelfth aspect of the present invention the apparatus guides a user who tends to exaggerate one side of an issue and to repress the other side of that issue, and to be stubborn in a time frame, so that he opens his mind to both sides of the issue and to changes over a period of time.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE DRAWING

FIG. 1 is a perspective view of an apparatus for enhancing decision-making in accordance with the first embodiment.

FIG. 2 is block diagram of the apparatus of FIG. 1.

FIG. 3 is a perspective view of an apparatus for enhancing decision-making in accordance with the second embodiment.

FIG. 4 is block diagram of the apparatus of FIG. 3.

FIG. 5 is a perspective view of an apparatus for enhancing decision-making in accordance with the third embodiment.

FIG. 6 is a perspective view of the apparatus of FIG. 5

FIG. 7a and FIG. 7b form a schematic drawing of the block diagram of the apparatus of FIG. 5.

FIG. 8 is a block diagram of a combined video game and an apparatus for enhancing decision-making in accordance with the fourth embodiment.

DESCRIPTION OF THE PREFERRED EMBODIMENT

Figure 7A:
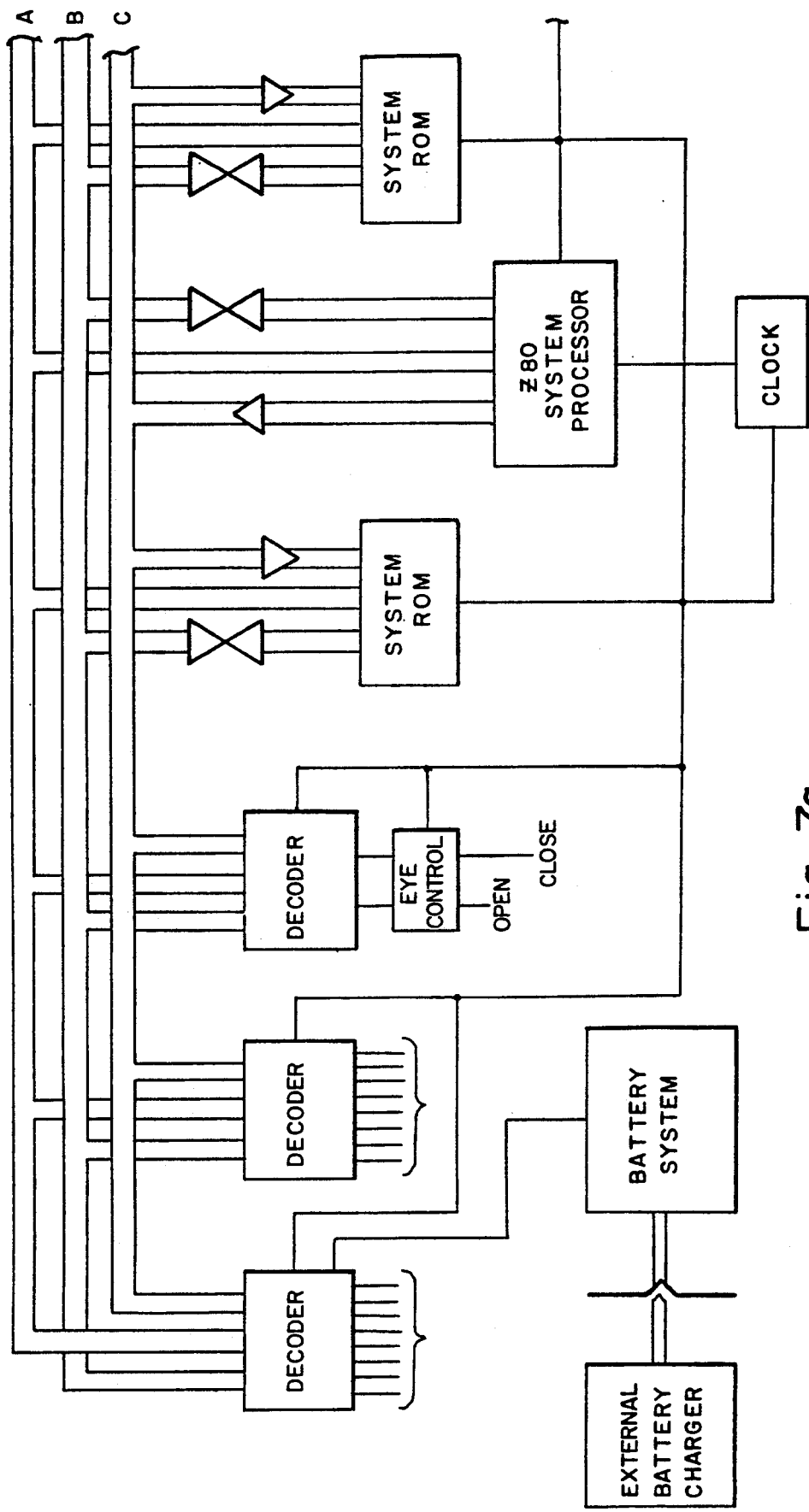

Referring to FIG. 1 an apparatus 10 for enhancing decision-making using left to right to left hemisphere guidance includes a housing 11, a first button 12 and a second button 13. The first and second buttons 12 and 13 are coupled to the housing 11. A user is given a first instruction to think about a subject until a first idea and a second idea, which is opposite to the first idea, related to the subject comes to his mind, then to make a choice from the first and second ideas. The use presses either the first button 12 or the second button 13 to designate his choice of either the first idea or the second idea. The user is given a second instruction to the user to look inside his head and ask himself if his chosen idea is right while he is inclined to a new discovery. The user is given a third instruction to see a picture of the subject in his head and while he is daydreaming the picture to listen for thoughts in his mind about how his chosen idea is right, then to listen for thoughts in his mind about how the other of the first and second ideas is right, then with both the first and second ideas in his mind to listen for changes over a period of time. The user is given a fourth instruction to verbalize at least one of his conclusions. The first and second buttons 12 and 13 are designated by a pair of opposite words from a group of pairs of opposite words consisting of positive and negative, good and bad, yes and no, know and do not know, accept and reject, you and I, up and down, past and future, right and wrong, like and dislike, should and should not, will and will not, can and can not, good and bad and good or bad, success and failure, this way and that way.

Referring to FIG. 2 in conjunction with FIG. 1 the apparatus 10 includes a first, second, third and fourth recording media 21 in which the respective instructions are recorded, a voice playback device 22 and a speaker 23. The voice playback device 22 is coupled to the housing 10. The first and second buttons 12 and 13 are electrically coupled to the voice playback device 22. The speaker 23 is electrically coupled to the voice playback device 22. The first, second, third and fourth recording media 21 are inserted into the voice playback device 22 in order to playback their respective instructions.

Referring to FIG. 3 an apparatus 110 for enhancing decision-making using left to right to left hemisphere guidance includes a housing 111, a button 112. The button 112 is coupled to the housing 111. A user is given a first instruction to think about a subject until a thought about the subject meaningful to the user comes to his mind and then to push the button 112. After he has pushed the button 112 the use is given a second instruction to look inside his head and ask himself if it is that way, while he is inclined to a new discovery. The user is given a third instruction to look at a picture of the subject in his head and while he is daydreaming the picture to listen for thoughts in his mind about how his thought is right, then to listen for thoughts in his mind about how his thought is not right and then with both sides in his mind to listen for changes over a period of time. The user is given a fourth instruction to verbalize at least one of his conclusions.

Referring to FIG. 4 in conjunction with FIG. 3 the apparatus 110 includes recording media 121 on which the respective instructions are recorded, a voice playback device 122 and a speaker 123. The voice playback device 122 is coupled to the housing 111. The button 112 is electrically coupled to the voice playback device 122. The speaker 123 is electrically coupled to the voice playback device 122. The recording media 121 is inserted into the voice playback device 122 in order to playback their respective instructions.

Referring to FIG. 5 in conjunction with FIG. 6 a trainer 210 for helping a child think a thought through to a balanced decision includes a housing 211, a first button 212 and a second button 213. The housing 211 has a front face 220 consisting of a mouth 221, a nose 222, a chin 223 and two eyes 224. The housing also has a head 225 which is composed of a drawing board 226 and a lid 227 which is openable. The first and second buttons 212 and 213 are disposed on the front face 220 adjacent to the mouth 221. A third button 228 is adjacent to the nose 222. A fourth button 229 is adjacent to the chin 223. There may be an introductory instruction to the child describing the source of all of the instructions and asking the user if he ever thought that he could do something and heard a doubting voice saying that he could not do it. There may also be another introductory instruction to the child saying "Ho, ho, ho, that was me. Want to play? Want to be friends?" A child is give a first instruction to open the lid 227 and draw or write about anything on the drawing board 226 and afterward to push the third button 228 which is adjacent to the nose 222. The first, second, third and forth buttons 212, 213, 228 and 229 are designated as good, bad, good and bad and I don't know, respectively. The child is given a second instruction to think about what the child has drawn or written about and to press one of the first, second, third and forth buttons 212, 213, 228 and 229 that best describes it. When the first button 212 is pressed, an instruction to close the lid 227 so that the child can play and look in his head and ask himself if it is good, then look at a picture about it in his head and daydreaming the picture listen for thoughts in his head how it is good, then listen for thoughts in his mind how it is bad, then with the good and bad in mind, listen for thoughts about what's going to happen. When the second button 213 is pressed, an instruction to close the head lid 227 so the child can play, then to look in his head and ask himself if its bad, then to look at a picture about it in his head and daydreaming the picture, listen for thoughts in his mind how its bad, then listen for thoughts in his mind how its good, then with the bad and good in mind, listen for thoughts about what's going to happen. When the third button 228 is pressed, an instruction to close the head lid 227 so the child can play, then to look in his head and ask himself if its good and bad, then to look at a picture about it in his head and daydreaming the picture, listen for thoughts in his mind how its good and bad, then listen for thoughts in his mind how its good or bad, then with both in mind, listen for thoughts about what's going to happen. When the fourth button 229 is pressed, an instruction to close the head lid 227 so the child can play, then to look in his head and ask himself if you don't know, then to look at a picture about it in his head and daydreaming the picture, listen for thoughts in his mind that he does not know, then listen for thoughts for thoughts about what's going to happen. There is a time delayed instruction to talk aloud about what he has heard in his mind. The trainer 210 may include a recording device which is coupled to the housing 211. What the child says aloud is recorded and played back aloud for the child to hear.

Referring to FIG. 7a and FIG. 7b in conjunction with FIG. 5 the trainer 210 includes a plurality of integrated circuits and other elements. All of the integrated circuits and the other elements are shown on the block diagram of the trainer 210.

Referring to FIG. 8 a combined video game and apparatus 310 for enhancing decision-making using left to right to left hemisphere guidance includes a housing 311, a video monitor 312, a computer 313, a start play button 314, stop play button 315, a memory device 316 in which instructions are recorded, a voice playback device 317 and a speaker 318. The video monitor 312 is disposed in the housing 311. The computer 313 is electrically coupled to the video monitor 312. Software 319 is placed in the computer 313 in order to form a video game. The start play button 314 and the stop play button 315 are coupled to the computer 313. A user is given a first instruction to press the start play button 314 to present a preview of the video game, observe an object from the preview and put a picture of the object in his head. The user is given a second instruction to look at the picture in his head and while daydreaming the picture press the start play button 314 again in order to commence action in the video game.

The apparatus 310 may also include a first button 321 and a second button 322 which are coupled to the housing 311. The user presses the stop play button 315 to stop playing the video game. The user is given a first instruction to think about what he is going to do next until a first idea and a second idea, which is opposite to the first idea, related to any subject comes to his mind, to make a choice from the first and second ideas and then to push either the first button 321 or the second button 322 to designate his choice of one of the first and second ideas. The user is given a second instruction to the user to look inside his head and ask himself if his chosen idea is right, while he is inclined to a new discovery. The user is given a third instruction to see a picture of the subject in his head and while he is daydreaming the picture to listen for thoughts in his mind about how his chosen idea about the subject is right, then to listen for thoughts in his mind about how his non-chosen idea about the subject is right, then with both the first and second ideas in mind to listen for changes over a period of time. The user is given a fourth instruction to verbalize at least one of his conclusions. The first and second buttons 321 and 322 are designated by a pair of opposite words from a group of pairs of opposite words consisting of positive and negative, good and bad, good and bad and good or bad, yes and no, up and down, you and I, past and future, know and do not know, accept and reject, right and wrong, like and dislike, should and should not, will and will not, can and can not.

In another embodiment an apparatus for enhancing decision-making using left to right to left hemisphere guidance includes a housing, one button which is coupled to the housing. A use is given a first instruction to think about a subject and to notice how he feels about it, then to push the feeling button. The user is given a second instruction to look inside his head and ask himself if he feels that way, inclined to a new discovery. The user is given a third instruction to the user to look at a picture of the subject in his head and while he is daydreaming the picture to notice that he does feel that way, then to look deeper inside himself where he does not feel that way, then to imagine changes in the picture that he wants and notice how he is feeling then. The user is given a fourth instruction to the user to verbalize his feelings about the subject. The apparatus may also include two buttons designated by a pair of opposite words. The user is given an instruction to think about a subject and to notice how you feel about it, then to push one of the two buttons that best describes how you feel about it. The user is given an instruction to look in his head and ask if he feels that way, inclined to a new discovery, then to look at a picture in his head about it and daydreaming the picture, notice that he does feel that way, then look deeper in himself where he does not feel that way, then imagine changes in the picture that he wants and notice how he feels then. The user is given an instruction to verbalize about his feelings. The two buttons are designated by a pair of opposite words from a group of pairs of opposite words consisting of positive and negative, good and bad, good and bad and good or bad, caring and uncaring, accepting and rejecting, appreciative and unappreciative, agreeable and disagreeable, friendly and unfriendly, glad for someone else and jealous of someone else, winner and loser, top and bottom, right and wrong, in control and out of control, happy and sad, peaceful and mad, know and do not know, accept and reject, you and I, right and wrong, like and dislike, should and should not, will and will not, can and can not. By using the apparatus the user gains a broaden understanding about his feelings and realizes a place inside of him where he does not feel the way he perceives that he feels. By imaging change in the picture in his head he is able to experience a resolution of his conflicting feelings.

A method for enhancing decision-making using left to right to left hemisphere guidance includes the steps of thinking about a subject until a thought about the subject meaningful to you comes to your mind and looking at a picture of the subject in your head and while you are daydreaming the picture to listen for thoughts in your mind about how your thought is right. The method also includes the steps of listening for thoughts in your mind about how your thought is not right and then with both sides in your mind to listen for changes over a period of time and verbalizing at least one of your conclusions.

From the foregoing it can be seen that apparati and method for enhancing decision-making have been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. An apparatus for enhancing decision making using left to right to left hemisphere guidance, said apparatus comprising:
   a. a housing;
   b. two buttons coupled to said housing wherein said two buttons are designated by a pair of opposite words from a group of pairs of opposite words consisting of positive and negative, good and bad, yes and no, know and do not know, accept and reject, right and wrong, like and dislike, should and should not, will and will not, can and can not, good and bad and good or bad, success and failure, this and that;
   c. a first recording medium with an instruction to a user to think about a subject until an issue related to the subject comes to his mind, then to make a choice from alternatives of the issue whereby the user presses one of said two buttons to designate his choice of one of the alternatives of the issue;
   d. a second recording medium with an instruction to the user to look inside his head and ask himself if he is right while he is inclined to a new discovery;
   e. a third recording medium with an instruction to the user to see a picture of the subject in his head and while he is daydreaming the picture to listen for thoughts in his mind about how he is right, then to listen for thoughts in his mind about the other side of the issue, then with both sides of the issue in this mind to listen for changes over a period of time;
   f. a fourth recording medium with an instruction to the user to verbalize at least one of his conclusions; and
   g. a voice playback device coupled to said housing, said voice playback device receives said first, second, third and fourth recording media in order to playback said instructions thereof.

2. A combined video game and apparatus for enhancing decision-making using left to right to left hemisphere guidance, said combined video game and apparatus comprising:
   a. a housing;
   b. a video monitor disposed in said housing;
   c. a computer electrically coupled to said video monitor;
   d. software placed in said computer in order to form a video game;
   e. a play button coupled to said computer;
   f. a first recording medium with an instruction to a user to press said play button to present a preview of said video game, observe an object from said preview and put a picture of said object in his head;
   g. a second recording medium with an instruction to the user to look at the picture in his head and while daydreaming said picture press said play button again in order to commence action in said video game; and
   h. a voice playback device coupled to said housing, said voice playback device receives said first and second recording media in order to playback said instructions thereof.

3. A combined video game and apparatus according to claim 2 whereby the user thinks through what he is going to do after he quits the video game until he develops a balanced attitude about it, said combined video game and apparatus includes:
   a two issue buttons coupled to said housing and a quit button coupled to said computer whereby the user presses said quit button to stop playing said vide game;
   b. a recording medium with an instruction to the user to think about what he is going to do next, then to push an issue button to designate his choice of one of the alternatives of the issue;

c. a recording medium with an instruction to the user to look inside his head and ask himself if it is that way, while he is inclined to a new discovery;

d. a recording medium with an instruction to the user to see a picture of the subject in his head and while he is daydreaming the picture to listen for thoughts in his mind about how his thought about the subject is right, then to listen for thoughts in his mind about how his thought about the subject is not right, then with both sides in his mind to listen for changes over a period of time and then to press the issue button again; and e. a recording medium with an instruction to the user to verbalize at least one of his conclusions.

4. A combined video game and apparatus according to claim 3 wherein said two buttons are designated by a pair of opposite words from a group of pairs of opposite words consisting of positive and negative, good and bad, good and bad and good or bad, yes and no, know and do not know, accept and reject, right and wrong, like and dislike, should and should not, will and will not, can and can not.

5. A combined video game and apparatus according to claim 2 whereby the user thinks through what he going to do after he quits the video game, until he develops a balanced attitude about it, said combined video game and apparatus includes:

a. one quit button coupled to said housing;

b. a recording medium with an instruction to the user to think about what he's going to do next until a thought meaningful to the user comes to his mind about what he is going to next and then to press the quit button;

c. a recording medium with an instruction to the user to look in his head and ask himself if its that way, inclined to a new discovery, then to look at a picture in his head about it, and daydreaming the picture, to listen for thoughts in his mind that his thought about what he is going to do next is right, then to listen for thoughts in his mind that his thought about what he is going to do next is not right, then with both sides in mind, to listen for changes over a period of time and then to press the quit button again; and d. a recording medium with an instruction to verbalize one of his conclusions.

6. A trainer for helping a child think a thought through to a balanced decision, said trainer comprising:

a. a housing having a front face of a mouth, nose, chin and two eyes, and a head composed of a drawing board and an opening lid;

b. at least two tooth disposed on said front face adjacent said mouth, a button adjacent the nose, and a button adjacent the chin whereby the trainer is turned on;

c. a first recording medium with an instruction to the child to open the head lid and draw or write about anything, then to push the nose button;

d. a second recording medium with an instruction to think about what the user has drawn or written about and to press one of said tooth buttons that best describes it;

e. a third recording medium with an instruction to the child to close said lid and then to look inside his head and ask himself if he is right, then to look at a picture of the subject in his head and while he is daydreaming the picture to listen for thoughts in his mind about how he is right, then to listen for thoughts in his mind about how he is not right, then with both sides of the issue in his mind to listen for changes over a period of time; and f. a fourth recording medium with an instruction to the user to verbalize at least one of his conclusions.

7. A trainer according to claim 6, said trainer comprising:

a. four buttons adjacent to said mouth whereby the child designates what he has drawn or written as good, bad, good and bad or I don't know;

b. when good button is pressed, a recording medium with an instruction to close the head lid so we can play and look in your head and ask himself if it is good, then look at a picture about it in your head and daydreaming the picture listen for thoughts in your head how it is good, then listen for thoughts in your mind how it is bad, then with the good and bad in mind, listen for thoughts about what's going to happen;

c. when bad button is pressed, a recording medium with an instruction to close the head lid so we can play, then to look in your head and ask himself if its bad, then to look at a picture about it in your head and daydreaming the picture, listen for thoughts in your mind how its bad, then listen for thoughts in your mind listen for thoughts about what's going to happen;

d. when good and bad button is pressed, a recording medium with an instruction to close the head lid so we can play, then to look in your head and ask himself if its good and bad, then to look at a picture about it in your head and daydreaming the picture, listen for thoughts in your mind how its good and bad, then listen for thoughts in your mind how its good or bad, then with both in mind, listen for thoughts about what's going to happen;

e. when I don't know is pressed, a recording medium with an instruction to close the head lid so we can play, then to look in your head and ask himself if you don't know, then to look at a picture about it in your head and daydreaming the picture, listen for thoughts in your mind that you don't know, then listen for thoughts in your mind that you do know, then with both in mind, listen for thoughts about what's going to happen;

f. a recording medium with a time delayed instruction to talk aloud about what you heard in your mind.

8. A trainer according to claim 7 wherein said trainer enhancer includes a recorder which records what the child says aloud and plays it back for the child to hear.

* * * * *